United States Patent [19]

Morimoto et al.

[11] Patent Number: 4,993,842
[45] Date of Patent: Feb. 19, 1991

[54] CALORIMETRIC DETECTION UNIT AND CALORIMETRIC MEMBER FOR CONDUCTION FLOW TYPE CALORIMETER

[75] Inventors: Satoshi Morimoto, Ushiku; Yoshio Tanaka, Tsukuba; Shojiro Ito, Tokyo, all of Japan

[73] Assignees: Agency of Industrial Science and Technology; Ministry of International Trade and Industry, Tokyo, Japan

[21] Appl. No.: 379,364

[22] Filed: Jul. 13, 1989

[30] Foreign Application Priority Data

Jul. 15, 1988 [JP] Japan ............................... 63-177732

[51] Int. Cl.$^5$ ............................................ G01K 17/06
[52] U.S. Cl. .......................................... 374/39; 374/29
[58] Field of Search ......................... 374/31, 32, 38, 29

[56] References Cited

U.S. PATENT DOCUMENTS

| | | | |
|---|---|---|---|
| 3,298,790 | 1/1967 | Benzinger | 374/31 X |
| 3,451,267 | 6/1969 | Wiegert et al. | 374/38 X |
| 4,085,613 | 4/1978 | Richard | 374/39 |
| 4,416,551 | 11/1983 | Kim | 374/31 |
| 4,484,471 | 11/1984 | Swithenbank et al. | 374/39 X |
| 4,511,263 | 4/1985 | Prosen | 374/38 |

OTHER PUBLICATIONS

23rd Forum on Calorimetry, Oct. 12-14, 1987, Japan Calorimetry Society, pp. 154 and 155.

*Primary Examiner*—Daniel M. Yasich
*Attorney, Agent, or Firm*—Oblon, Spivak, McClelland, Maier & Neustadt

[57] ABSTRACT

A detection unit essentially consists of (I) a plurality of calorimetric detection elements for the conduction flow type calorimeter each consisting essentially of a plurality of thermopiles severally supported on heat sinks and (II) a heat insulating member interposed between the adjacent calorimetric detection elements. A calorimetric measuring member for a conduction flow type calorimeter comprises a pair of the detection units and a sample pipe fixed in place between the pair of detection units.

2 Claims, 4 Drawing Sheets

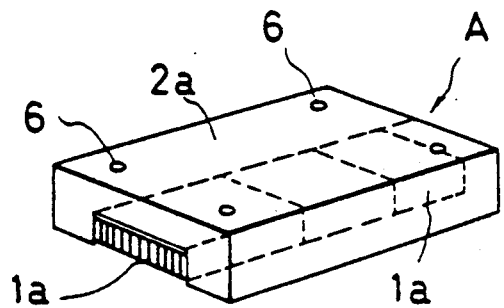
FIG. 1A
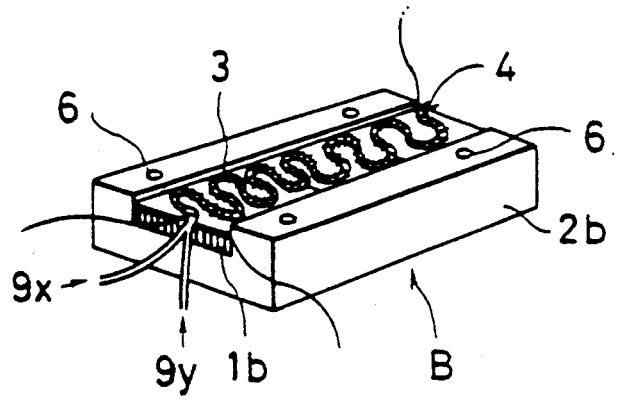
FIG. 1B
FIG. 2
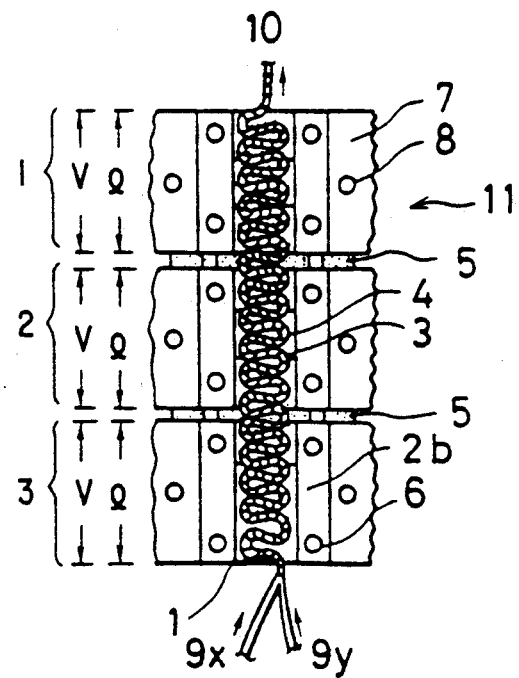

CALORIMETRIC DETECTION UNIT AND CALORIMETRIC MEMBER FOR CONDUCTION FLOW TYPE CALORIMETER

BACKGROUND OF THE INVENTION

1. Field of the Invention

This invention relates to a calorimetric detection unit and a calorimetric member for a precision calorimeter for the measurement of reaction heat. More particularly, this invention relates to a calorimetric detection unit and a calorimetric member for a conduction flow type calorimeter for accurate continuous measurement over the course of time of the amount of heat generated and absorbed during the mixture, dilution, and reaction between two gases, liquids, or solutions.

Advances in measuring machines and devices are contributing greatly to the elucidation of various chemical and physical phenomena and functions. The present invention constitutes one such advance in the field of science in which the present inventors specialize in that enables analysis of the functions of biomolecules, such as proteins and nucleic acids, and blood cells. For example, this invention makes it possible to detect with heretofore unattainable accuracy subtly variations in the amounts of heat of reaction minute amounts of heat produced upon the reaction and/or mixing of biomolecules and blood cells and of a time-course change in these amounts. It is, therefore, expected to contribute to the investigation of the causes of diseases in the fields of diagnosis and therapy.

2. Prior Art Statement

Calorimeters fall roughly into three types, i.e. the adiabatic type, the isothermal type, and the conduction type. The calorimetric detection unit and the calorimetric member contemplated by the present invention are intended for use in conduction flow type calorimeters. The name "conduction type" implies that amounts of heat are detected by means of a thermopile concurrently serving as a heat conductor. By "flow type" is meant that the system is for detecting and measuring amounts of heat generated by a pair of fluids such as gases, liquids, or solutions when they are introduced into a single sample-passing pipe laid on a thermosensitive element. Calorimeters of this type are frequently used in experimental studies because they facilitate detection of the amount of heat, simplify the operation, and achieve quick temperature equilibration.

The conventional conduction flow type calorimeter is constructed by superposing a metallic plate of high thermal conductivity on a detecting element and helically disposing thereon a sample-passing pipe for fluids so as to enclose and immobilize the metallic plate or by having the sample-passing pipe helically wound on the periphery of a metallic cylinder of high thermal conductivity. The amount of heat measured by this calorimeter, therefore, inevitably includes a component due to the change of temperature taking place in the metallic plate or metallic cylinder. This calorimeter thus measures the change in temperature of an article having a large thermal capacity as compared with the small amount of sample fluid and, therefore, does not allow measurement with high sensitivity.

Further, the conventional conduction flow type calorimeter has been incapable of continuously measuring change in amount of heat over the course of time.

OBJECT AND SUMMARY OF THE INVENTION

The object of this invention is to provide a calorimetric member and a calorimetric detection unit as a component of the calorimetric member for a conduction flow type calorimeter capable of measuring amounts of heat quickly and with high sensitivity and further capable of continuously measuring changes in the amount of heat over the course of time.

The inventors conducted a study for realizing the aforesaid object and, as a result, accomplished this invention.

Specifically, according to the present invention there is provided a calorimetric detection unit for a conduction flow type calorimeter, comprising a plurality of calorimetric detection elements each comprising two members, the two members each comprising an inner heat sink having one set of thermopiles supported on an inner side thereof, and an outer heat sink of a shape substantially semicircular in lateral cross section and having a recess for accommodating therein the inner heat sink, the two members being assembled into a calorimetric detection element by facing two sets of thermopiles each other across a given space and enclosing two inner heat sinks by two outer heat sinks, a plurality of insulating members each interposed between adjacent ones of the plurality of calorimetric detection elements for joining the adjacent calorimetric detection elements with each other therethrough, with given spaces between the facing thermopiles constituting a continuous space, and a sample pipe having an electric resistance heating wire wound thereon and laid in a zigzagged pattern within the continuous space, whereby individual or total calories of the plurality of calorimetric detection elements are measured.

Further, in the present invention, thermocouples, thermoelectric piles or PN semiconductors arranged in series connection are advantageously used as thermopiles. The sample pipe is zigzagged and has an electric resistance wire wound thereon.

The above and other objects and features of the invention will become more apparent from the following detailed description with reference to the accompanying drawings.

BRIEF DESCRIPTION OF THE DRAWINGS

FIG. 1A is a perspective view illustrating one of the two members constituting a calorimetric detection element to be used in a calorimetric detection unit for the conduction flow type calorimeter according to this invention, and FIG. 1B is a perspective view illustrating the other of the two members, with a sample pipe placed thereon.

FIG. 2 is a cross section illustrating the structure of a calorimetric detection unit of this invention which is composed of three calorimetric detection elements.

DETAILED DESCRIPTION OF THE PREFERRED EMBODIMENTS

Figure 3:
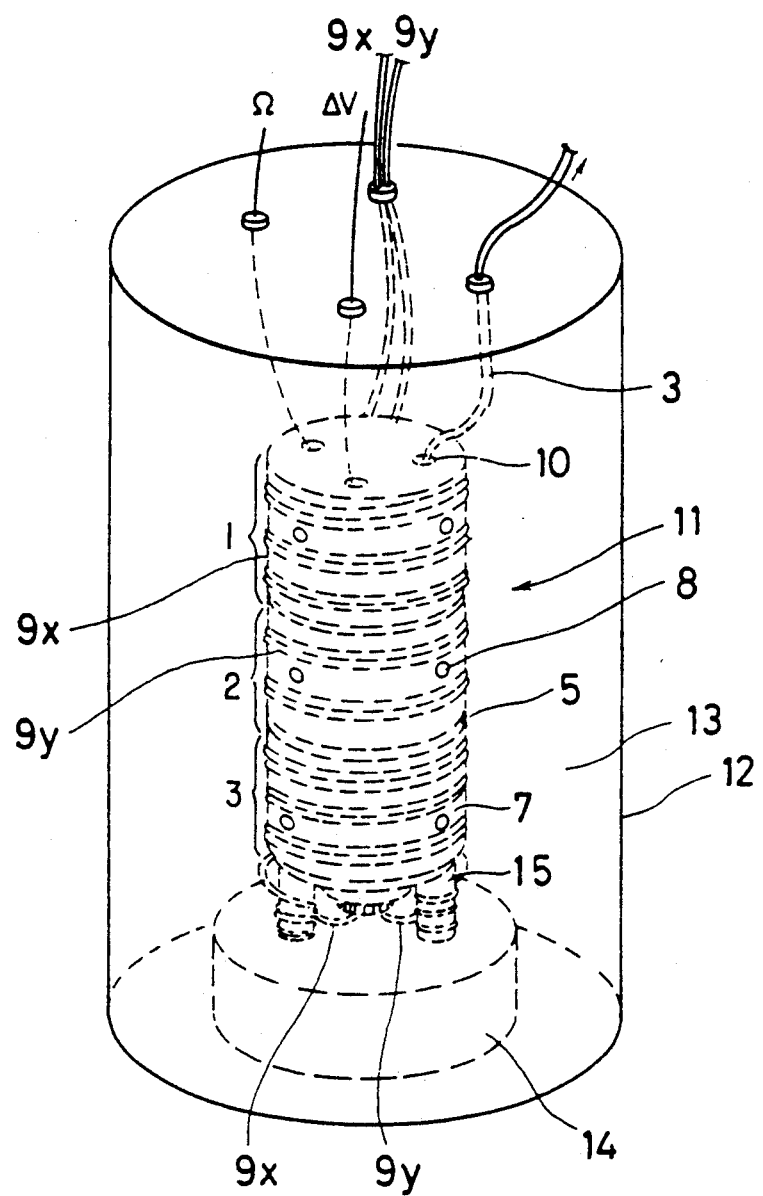
FIG. 3 is a perspective view illustrating the conduction flow type calorimeter incorporating therein the calorimetric detection unit of the present invention.

The present invention will now be described in detail below.

The calorimetric detection unit of this invention is used for the conduction flow type calorimeter.

The detection unit is composed of a plurality of calorimetric detection elements, with a heat insulating member interposed between the adjacent calorimetric detection elements.

The calorimetric detection element is composed of two members each having thermopiles arranged linearly in series connection and supported on an inner sink which is enclosed by an outer sink. Since the number of such thermopiles can be freely selected, the calorimetric detection element can acquire a sufficiently large thermoelectromotive force. The calorimetric detection unit of this invention has a sample pipe interposed between the opposed thermopiles of the two members and provided with an electric resistance wire wound around the periphery thereof. Owing to this construction, the calorimetric detection unit can measure the heat of reaction of the fluids with high sensitivity. The sample pipe is disposed in a suitably bent form.

As a plurality of detection members can be connected in series via interposed heat insulating members, it is possible to obtain a sample pipe of sufficient length to enable heat detection to be conducted from the time that two fluids are mixed to the time that the reaction between the fluids is completed.

Since the plurality of calorimetric detection elements are partitioned from one another by heat insulating members, they are capable of independently measuring the amount of heat. They are, therefore, capable of directly measuring changes in the amount of reaction heat continuously over the course of time.

The conventional calorimeters of this type have only been capable of measuring the amount of heat between the inlet position and the outlet position for the fluids. They have been incapable of measuring the change in the amount of heat.

Thermopiles usable in this invention are those generally used in calorimeters of various sorts such as, for example, thermocouples, thermoelectric piles, and PN semiconductors arranged in series connection.

In this invention since the sample pipe disposed between the opposed thermopiles of the members is laid in a zigzagged pattern as described above, it permits the fluids under test to be mixed amply as compared with a sample pipe which is helically laid or wound spirally on the periphery of a cylinder. Further, since the electric resistance wire for the measurement of the amount of heat is wound in a coiled pattern directly on the sample pipe, the calorimeter having the calorimetric unit of this invention measures the amount of heat with high accuracy as compared with the conventional flow type calorimeter having an electric resistance wire fixed at one point of the conductor, for example.

Now, the present invention will be described below on the basis of the drawings illustrating a typical structure of the calorimetric detection unit of the present invention.

FIG. 1A and FIG. 1B illustrate members A and B each having three thermopiles 1a or 1b supported within an inner sink (a constant temperature bath of large thermal capacity or a heat storage) 2a or 2b. The inner sinks 2a and 2b are disposed face to face so that their respective thermopiles 1a and 1b face each other and are enclosed by two outer heat sinks 7 of a shape substantially semicircular in lateral cross section and each having a recess for accommodating the inner heat sink 2a or 2b therein, thereby constituting a calorimetric detection element. A plurality of such calorimetric detection elements are serially joined, with heat insulating members 5 interposed between the adjacent calorimetric detection elements and a sample pipe 3 interposed between the opposed thermopiles 1a and 1b, thereby constituting a calorimetric detection unit. The heat insulating member 5 is made of, for example, a polyethylene fluoride (such as Teflon). An electric resistance wire 4 is wound on the sample pipe 3 into which conduits 9x and 9y for the passages of fluids to be mixed are combined.

FIG. 2 is a cross section illustrating a calorimetric detection unit of the present invention which comprises three calorimetric elements I, II and III which are joined to one another through the insulating members 5. The inner sinks 2 have screw holes 6 bored therein for fastening themselves with bolts, and the outer sinks 7 have screw holes 8 bored therein for fastening themselves with bolts.

As illustrated in FIG. 2, the sample pipe is laid continuously through the three elements (I, II and III). Reference numeral 10 stands for an outlet for the reaction fluid. These three elements are provided with respective electric resistance wires. This means that the elements are independently capable of measuring the amount of heat.

As the thermopiles, thermocouples, thermoelectric piles, or PN semiconductors arranged in series connection are used. As a concrete example, P/N FC 0.6-66-06L produced by MELCOR Corp. may be cited. The thermopiles in this case produce an electromotive force in the range of 5 to 6 mV/°C. per thermopile. When a total of six elements are arranged in series connection as illustrated in FIG. 1 (the elements A, B use a total of 6 thermopiles), the total electromotive force is in the range of 30 to 36 mV/°C.

Preferably, the electric resistance wires are Manganin alloy wires or Nichrome alloy wires, which are well known in the art. Materials usable for the sample pipe include resins, such as polyethylene and polypropylene, and metals.

FIG. 3 illustrates a typical measuring device for actual use incorporating the calorimetric detection unit 11 of the present invention. The calorimetric detection unit 11 is fixed on a base 14 through legs 15 inside a hollow cylindrical container 12 (made of stainless steel, for example). A pair of conduits 9x and 9y into which two kinds of fluids flow are wound on the periphery of the calorimetric detection unit 11 downwardly and, at the bottom of the unit 11, combined into the sample pipe 3. The sample pipe 3 is passed between the opposed thermopiles 1a and 1b in a zigzagged pattern to adjust the mixed fluid to have a prescribed temperature and is taken out of the outlet 10.

Now, the present invention will be described more specifically hereinbelow with reference to working examples.

EXAMPLE 1

In the calorimetric detection unit of this invention illustrated in FIG. 3 (using calorimetric detection elements of the construction of FIG. 2), one of the calorimetric detection elements was exposed to the standard amount of electrically generated heat and the other calorimetric detection elements were tested for possible effect of the heat. The test was conducted under the following conditions.

Thermopile: Thermomodule (produced by MELCOR Corp. and marketed as "P/N FC 0.6-66-062")

Electromotive force of thermopiles: 30 to 36 mV/°C. (5 to 6 mV/°C. per thermopile)

Heat insulating member: Polytetrafluoroethylene sold under the trademark "Teflon") plate 2 mm in thickness Sample pipe: Made of polyethylene and measuring 0.86 mm in inside diameter, 1.27 mm in outside diameter, and 72.4 cm in length Heat sinks 2a, 2b, 7: Both of aluminum Container 12: Made of stainless steel The container 12 was immersed in a constant temperature bath kept accurately within ±1/1,000° C. Further, the hollow portion 13 of the container 12 was filled to capacity with perfluorocarbon (produced by Sumitomo Electric Industries, Ltd. and marketed under tradename "Florinate") to prevent entry of the water used in the constant temperature bath. Water was introduced through the inlets of two conduits 9x and 9y at a flow volume of 6 ml/hr. The standard amount of heat (5 μJ/second) was applied separately to the component calorimetric detection elements of I, II, and III. The remaining detection elements not exposed to the heat were tested for possible effects of the heat.

Figure 4A:
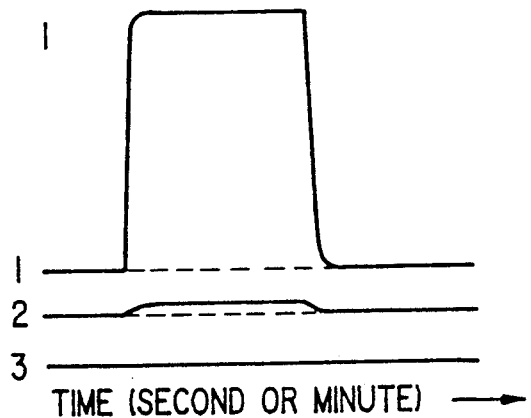
FIGS. 4A, 4B and 4C are diagrams showing the results of the measurement conducted in Example 1.
Figure 4B:
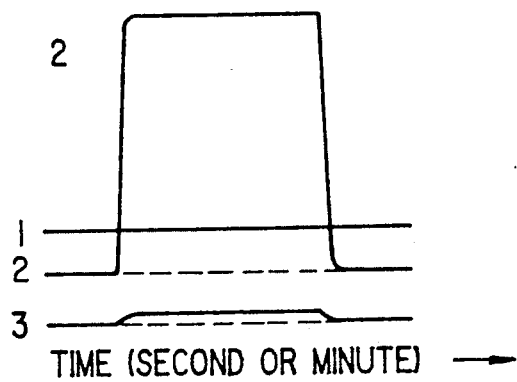
Figure 4C:
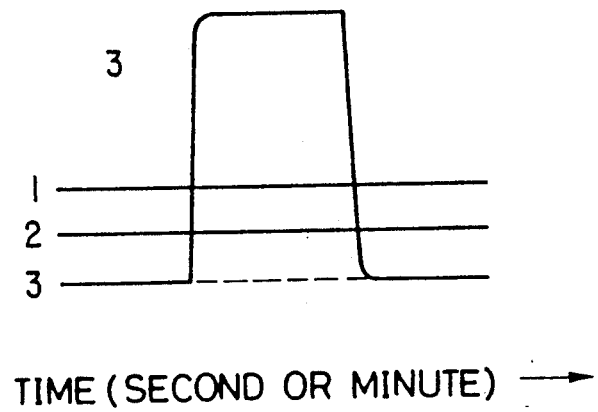

The results of the test were as shown in FIG. 4.

In the diagram, (I), (II), and (III) represent the thermoelectromotive forces exhibited by the elements I, II, and III when the heat was applied separately to these elements. The diagram indicates that the elements not exposed to the heat were substantially unaffected.

EXAMPLE 2

The heats of reactions in a protein system (such as sodium pump protein with ATP) and in a blood cell system (such as human plasma cell with a chinese medicine (juzendaihoy)) were measured using a calorimetric detection unit of the structure shown FIG. 3.

Figure 5:
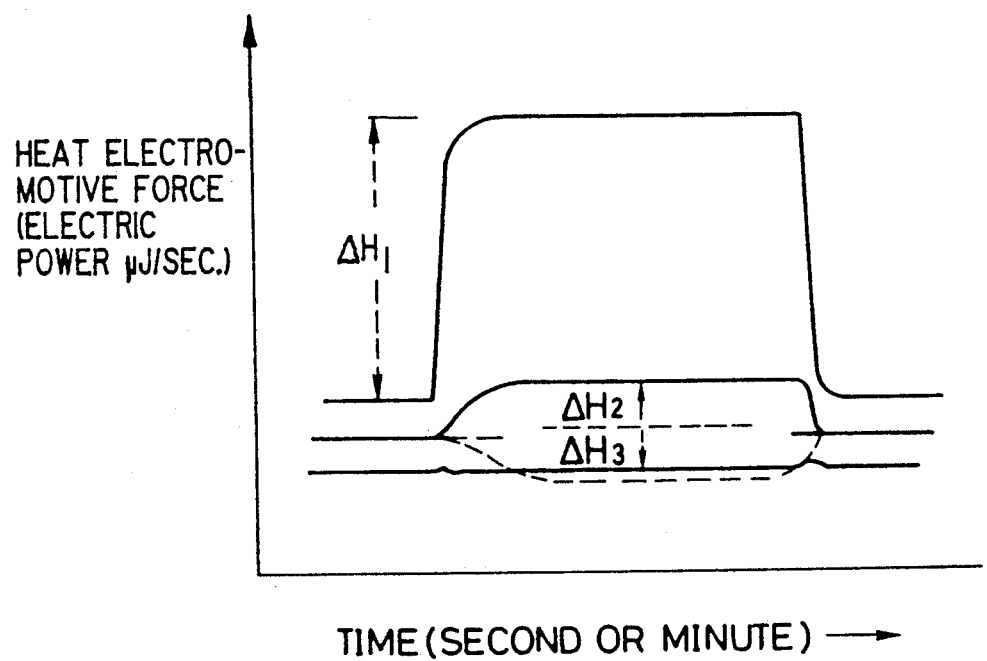
FIG. 5 is a diagram showing the results of the measurement conducted in Example 2.

The sample pipe was wound with a 50 Ω Manganin alloy wire, which was supplied with an electric current of 1 mA. The aforesaid liquids were fed into the sample pipe at flow volumes in the range of 6 to 60 ml/hr and the electromotive force generated in each of the detection elements I, II, III was measured. The results of the measurement for the respective elements are shown in FIG. 5.

Element I generated the electromotive force $\Delta H_1$ and the major part of the reaction was completed in this element. The mixture of liquids then passed into element II, which generated the electromotive force $\Delta H_2$ in the case of the exothermic blood cell system reaction and the electromotive force $\Delta H_3$ in the case of the endothermic protein system reaction. From the values it will be understood that only a small amount of heat was involved. The fluids then advanced to element III, which produced no electromagnetic force at all.

Thus when the liquids are passed progressively through the elements I, II, III, it becomes possible to measure time-course changes in the heat electromotive force.

Actually, the changes detected in the elements II and III at the aforementioned flow volume correspond to those at respective intervals of several seconds and some tens of seconds following the outset of mixture or reaction. Though the base lines (standard states) varied with the flow volume, the amounts of exotherm and those of endotherm could be detected with high repeatability. Changes over a wide range could be measured over the course of time by suitable variation of the flow volume. While the flow type calorimeters currently available on the market have detection sensitivities on the order of 1 μW, the calorimeter using the detection unit according to this invention allows highly accurate measurement with extremely high sensitivity down to 0.1 μW or even below.

What is claimed is:

1. A calorimetric detection unit for conduction flow type calorimeter, comprising:
   sample pipe means;
   a plurality of calorimetric detection elements each comprising two members;
   said two members each comprising an inner heat sink having one set of thermopiles supported on an inner side thereof, and an outer heat sink of a shape substantially semicircular in lateral cross section and having a recess for accommodating therein said inner heat sink;
   said two members being assembled into a calorimetric detection element by facing two sets of thermopiles opposite to each other across a given space and having said sample pipe means passed therethrough and enclosing two inner heat sinks by two outer heat sinks;
   a plurality of insulating members each interposed a preselected distance between adjacent ones of said plurality of calorimetric detection elements for insulating and spacing adjacent calorimetric detection elements from each other such that said sample pipe means passes through each of said insulating members; and
   an electric resistance heating wire wound around said sample pipe means and wherein said sample pipe means is laid in a zigzagged pattern;
   whereby individual or total calories of said plurality of calorimetric detection elements are measured.

2. A calorimetric detection unit according to claim 1, wherein said thermopiles are those of one kind selected from the group consisting of thermocouples arranged in series connection, thermoelectric piles, and PN semiconductors arranged in series connection.

* * * * *